US007494612B2

(12) United States Patent
Kelley

(10) Patent No.: US 7,494,612 B2
(45) Date of Patent: Feb. 24, 2009

(54) MEDICAL BALLOON FOLDING METHOD AND TOOLING

(75) Inventor: Greg S. Kelley, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 860 days.

(21) Appl. No.: 10/978,113

(22) Filed: Oct. 29, 2004

(65) Prior Publication Data

US 2006/0091585 A1    May 4, 2006

(51) Int. Cl.
    *B29C 53/00* (2006.01)
(52) U.S. Cl. .............. 264/339; 264/295; 264/209.3; 264/285; 425/391; 425/392; 604/96.01; 606/194
(58) Field of Classification Search ............ 264/239, 264/293, 320, 323, 392; 425/392, 391; 606/194; 269/265; 156/204; 604/96.01
    See application file for complete search history.

(56) References Cited

U.S. PATENT DOCUMENTS

| 4,192,313 | A | * | 3/1980 | Ogami .................. 606/207 |
|---|---|---|---|---|
| 5,112,305 | A | | 5/1992 | Barath et al. ............... 604/96 |
| 5,147,302 | A | | 9/1992 | Euteneuer et al. .......... 604/103 |
| 5,209,799 | A | | 5/1993 | Vigil ........................ 156/156 |
| 5,226,887 | A | | 7/1993 | Farr et al. .................. 604/96 |
| 5,242,397 | A | | 9/1993 | Barath et al. ............... 604/96 |
| 5,320,634 | A | | 6/1994 | Vigil et al. ................ 606/159 |
| 5,616,149 | A | | 4/1997 | Barath ...................... 606/159 |
| 5,681,281 | A | | 10/1997 | Vigil et al. ................ 604/96 |
| 5,783,227 | A | | 7/1998 | Dunham .................... 425/318 |
| 6,013,092 | A | | 1/2000 | Dehdashtian et al. ....... 606/194 |
| 6,033,380 | A | | 3/2000 | Butaric et al. .............. 604/96 |
| 6,123,718 | A | * | 9/2000 | Tu et al. .................... 607/113 |
| 6,126,652 | A | | 10/2000 | McLeod et al. ............. 606/1 |
| 6,283,743 | B1 | | 9/2001 | Traxler et al. .............. 425/391 |
| 6,623,689 | B2 | | 9/2003 | Traxler et al. .............. 264/573 |
| 6,632,231 | B2 | * | 10/2003 | Radisch, Jr. ................ 606/159 |
| 2004/0059290 | A1 | * | 3/2004 | Palasis .................. 604/101.01 |

OTHER PUBLICATIONS

Delorme, Sebastien, Denis Laroche, Robert DiRaddo and Jean Buithieu, "Modeling Polymer Balloons for Angioplasty: From Fabrication to Deployment", Sep. 14, 2004, Society of Plastics Engineers, vol. 3, p. 3375.*
New England Catheter Corporation, http://web.archive.org/web/20041014222717/http://necatheter.com/catheter.asp, Oct. 2004, www.archive.org.*
Merriam-Webster, http://www.merriam-webster.com/dictionary/end.*

* cited by examiner

*Primary Examiner*—Christina Johnson
*Assistant Examiner*—Galen Hauth
(74) *Attorney, Agent, or Firm*—Vidas, Arrett & Steinkraus, P.A.

(57) ABSTRACT

A tool for imparting a plurality of folds to a balloon comprises a housing, which defines a passage therethrough. The passage has a longitudinal axis and a first opening at a first end of the passage, and a second opening at a second end of the passage. The passage has an inner surface, which defines a plurality of peaks and valleys, wherein the height of each peak is greater at the first end of the passage than at the second end of the passage and the height of each valley is greater at the first end of the passage than at the second end of the passage.

22 Claims, 9 Drawing Sheets

MEDICAL BALLOON FOLDING METHOD AND TOOLING

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Medical balloons are used in the body in a variety of applications including as dilatation devices for compressing plaque and for expanding prosthetic devices such as stents at a desired location in a bodily vessel. Because it is typically necessary for the balloon to traverse a tortuous anatomy as it is being delivered to the desired location in the bodily vessel, it is desirable for the balloon to assume as low a profile as possible.

The folding of medical balloons in order to reduce the cross sectional area or profile of the balloon is a common industry practice. Balloons may also be folded in order to enhance re-fold characteristics of the balloon during deflation.

In some applications balloons are known to be equipped with blades, injectors, protrusions, atherotomes and/or other surface features.

Devices used for imparting the desired folded configuration vary. Some devices fold the balloon by imparting an inward radial force about the periphery of the balloon using a plurality of rigid blades and/or jaws which are distributed about the periphery of the balloon.

In some cases it is necessary to crease the balloon prior to folding. In such cases the balloon is first creased by a tool having a pair of jaws in a "pliers" style configuration, which may be compressed about the balloon to place creases in the balloon in preparation for the subsequent formation of the folds. The balloon may then be placed in a crimping or folding device, which typically employs a plurality of blades that move radially inward against the balloon, during which the balloon may be partially inflated, to impart the balloon with a plurality of wings that may be folded about the longitudinal axis of the balloon. Methods and devices described above are often limited to specific types and sizes of balloons as different size balloons will typically require different numbers and sizes of folds to accommodate the differing amount of balloon material.

In light of the above there remains a need to provide additional alternatives to crease and fold a balloon.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment the invention is directed to a tool for reducing the profile of an expandable member such as a medical balloon. At least on embodiment of the invention is directed to a method of using such a tool.

In at least one embodiment the tool defines a passage which has a substantially frusto-conical shape, with a large opening at one end and a small opening at the other.

In some embodiments the inner surface of the passage comprises a plurality of peaks and valleys. The peaks are configured to push against a balloon to form creases in the balloon surface as the balloon is advanced through the passage from the large opening to the smaller opening. The valleys are configured to receive balloon material in the form of folds that are created as a result of the creasing of the balloon and the gradually reducing diameter of the passage.

The passage may be configured to include about 3 to about 50 peaks and about 3 valleys to about 50 valleys.

In some embodiments the passage has one or more protrusion channels to accommodate passage of surface features of the balloon with out detriment thereto. The protrusion channels may be configured to receive one or more blades, injectors, atherotomes, or other protrusions. In some embodiments the balloon may be provided with at least one therapeutic agent thereon.

These and other embodiments which characterize the invention are pointed out with particularity in the claims annexed hereto and forming a part hereof. Reference can be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
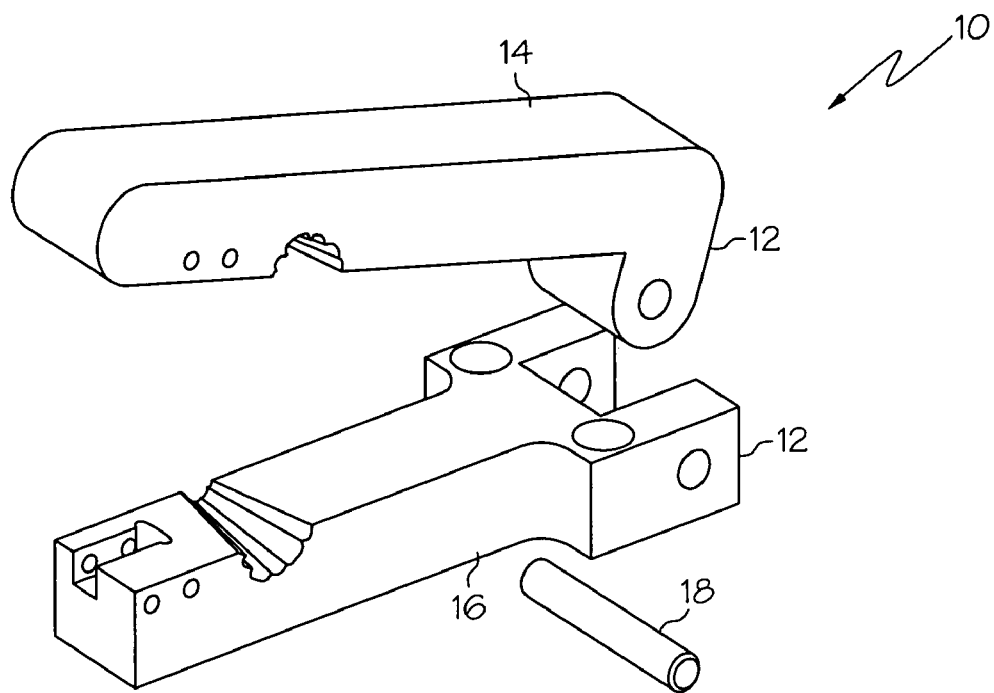
FIG. 1 is a perspective/exploded view of an embodiment of the invention comprising a balloon folding tool.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
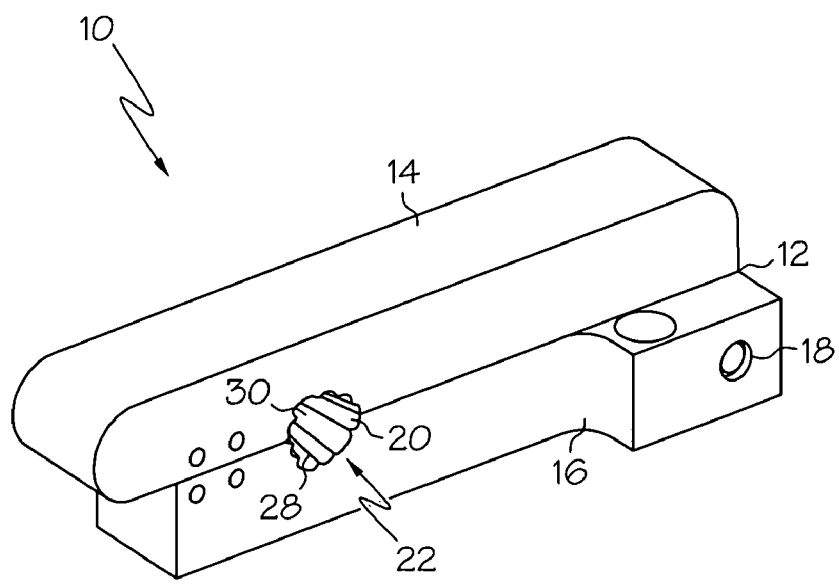
FIG. 2 is a perspective view of the tool shown in FIG. 1, assembled.
Figure 3:
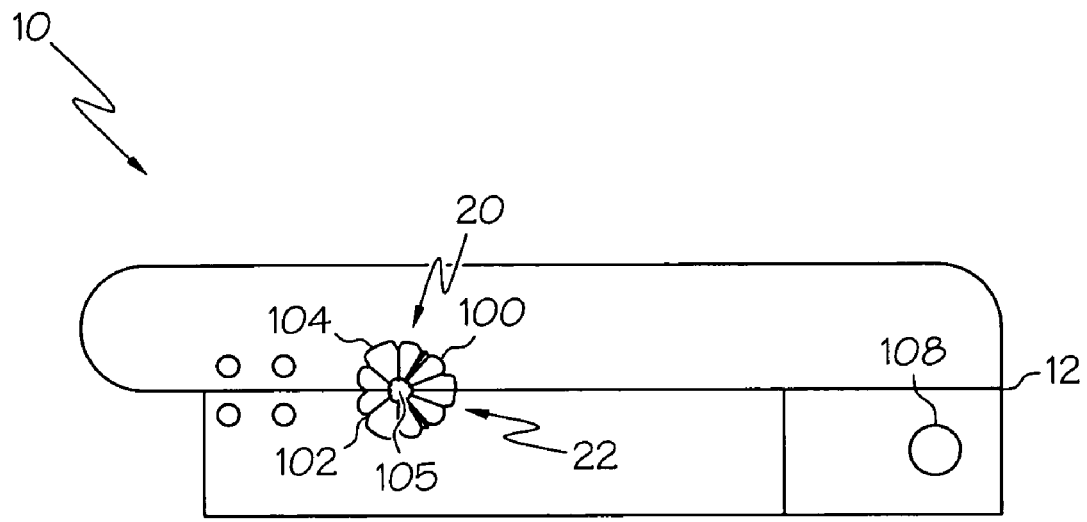
FIG. 3 is a frontal view of the tool shown in FIG. 2.

In at least one embodiment, the invention is directed to a balloon folding tool 10, such as is shown in FIGS. 1-4. The tool 10 comprises a housing 12, which in the embodiments depicted herein may further comprise two complementary segments 14 and 16. As is illustrated in FIGS. 1-3 the first segment 14 and the second segment 16 may be pivotally engaged about a pivot member 18, however the segments may be otherwise moveably engaged. In some embodiments the segments 14 and 16 may be fixedly engaged to one another, or alternatively the housing 12 may be a single piece design.

Figure 4:
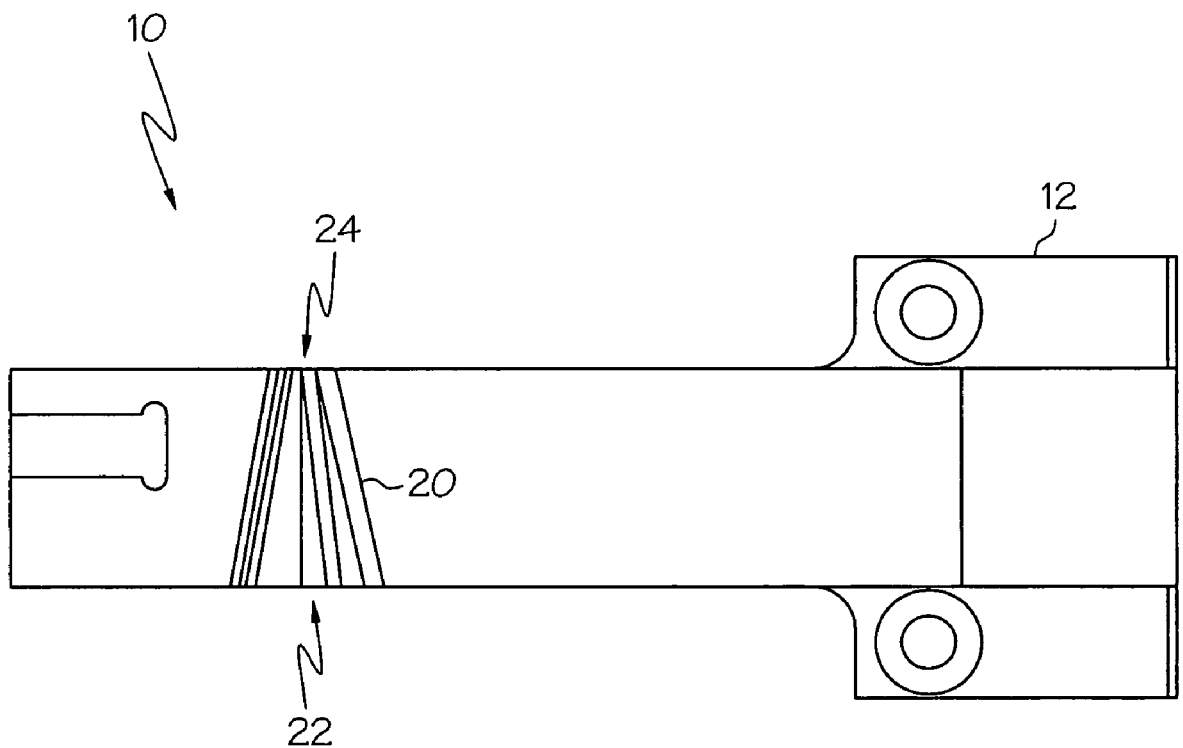
FIG. 4 is a side view of the tool shown in FIG. 2.

When the segments 14 and 16 of the tool 10 are assembled, such as in the manner depicted in FIGS. 2-3 or otherwise, the housing 12 defines a folding passage 20. Passage 20, as is best shown in FIG. 4, is a substantially frusto-conical shaped passage which extends through the housing 12. One end of the passage 20 is defined by a first opening 22 which tapers down to narrower second opening 24 at the second end of the passage 20. In operation a balloon 100 (such as is described in greater detail below and shown in FIGS. 5-17b) in a prefolded state is introduced into the passage 20, through the first or larger opening 22 and advanced through the passage where it exits out the smaller or second opening 24. By passing the balloon 100 through the passage 20, the balloon is imparted with a plurality of folds 102 which may then be wrapped about the central lumen 104 of the balloon 100 in any manner desired.

Figure 5:
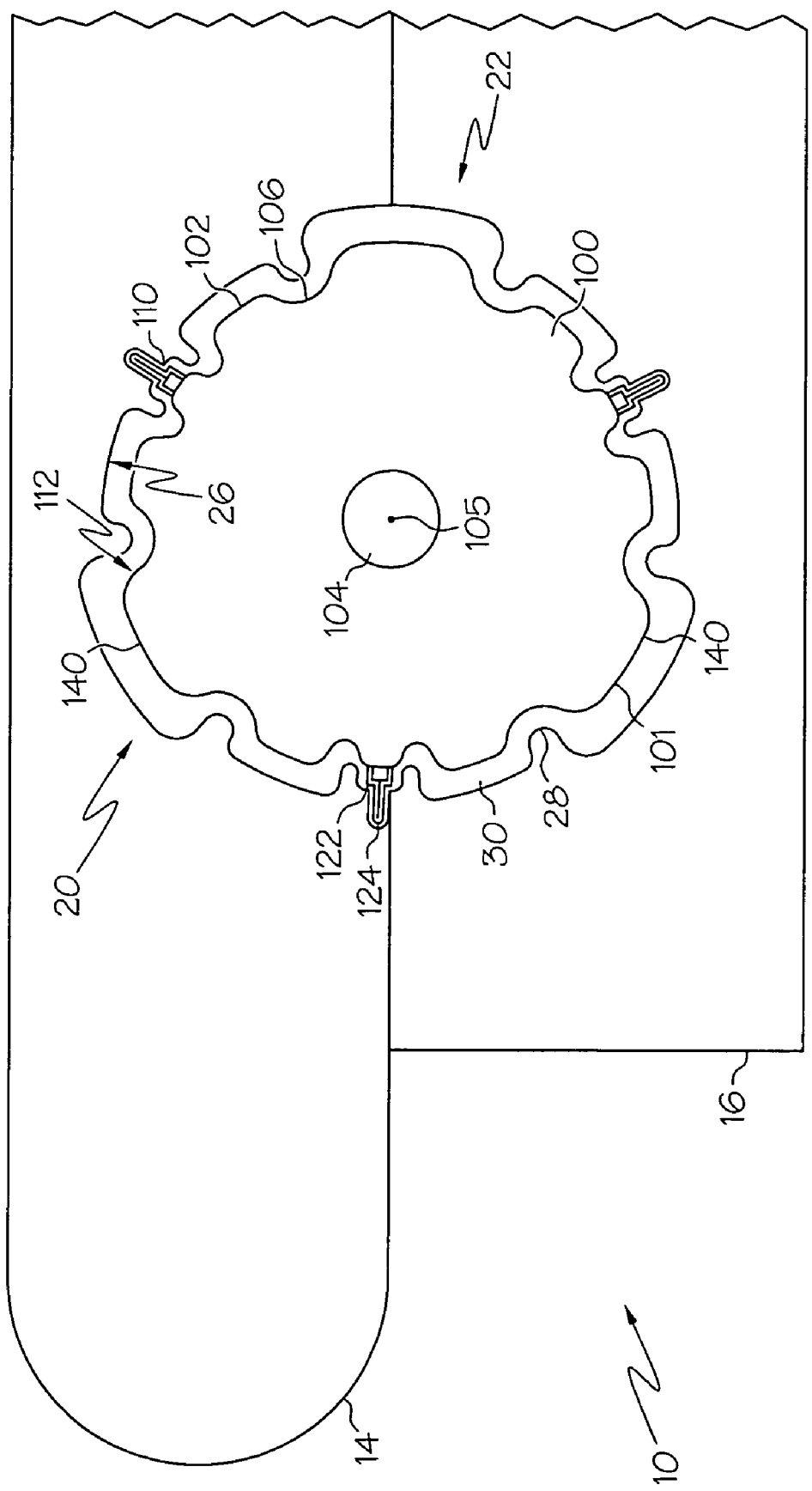
FIG. 5 is an enlarged schematic view of the large end opening of the tool shown in FIG. 2.
Figure 6:
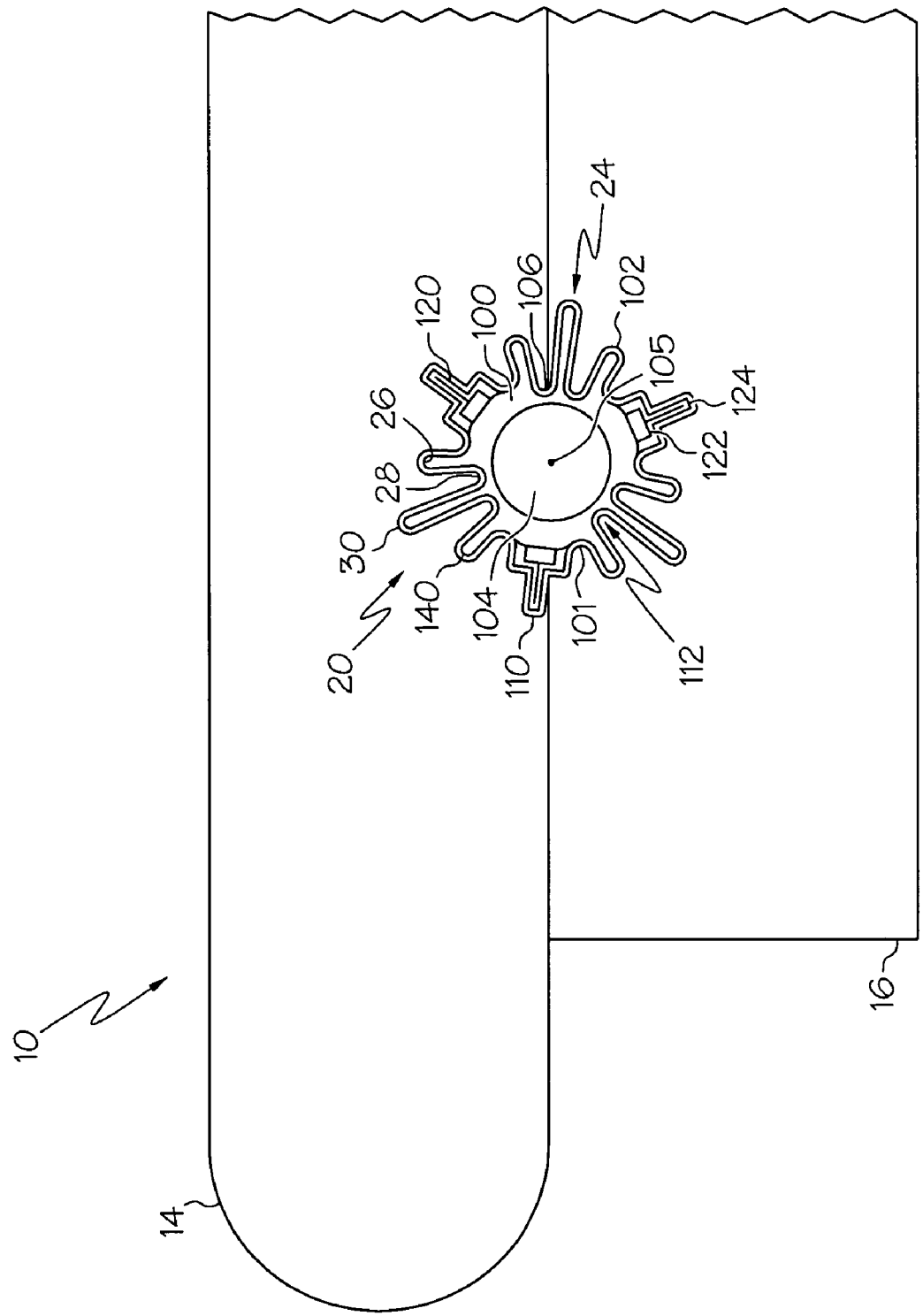
FIG. 6 is an enlarged schematic view of the small end opening of the tool shown in FIG. 2.
Figure 7:
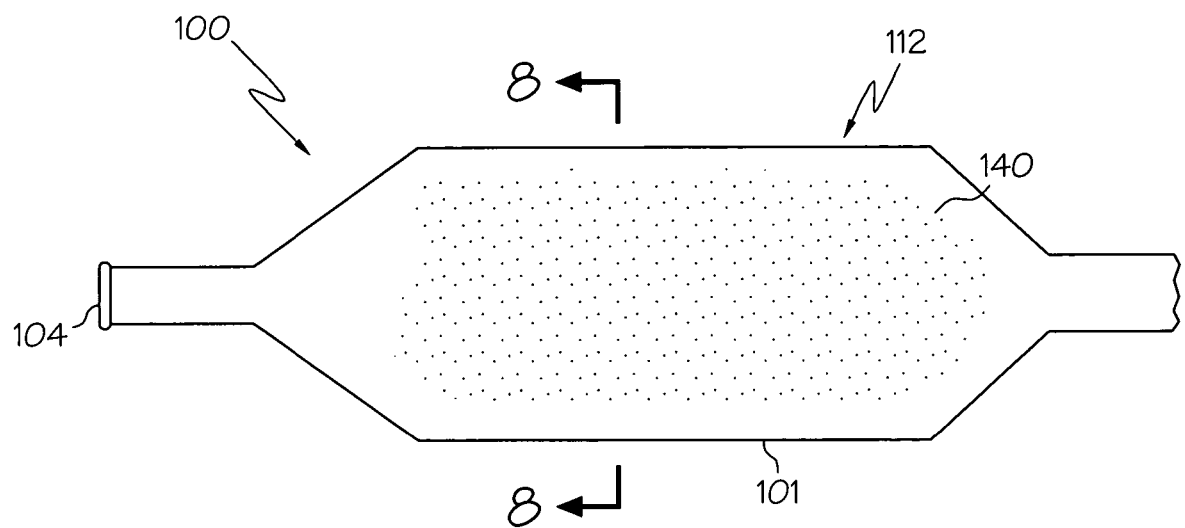
FIG. 7 is a longitudinal side view of a balloon prior to being folded by the folding tool.
Figure 8:
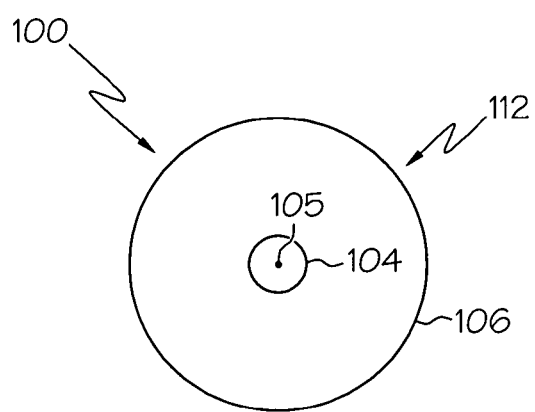
FIG. 8 is a cross-sectional view of the balloon of FIG. 7.

As is shown in FIG. 2, and also FIGS. 5 and 6, the interior surface 26 of the passage 20 is provided with a plurality of peaks 28 and valleys 30 which will tend to crease and fold a balloon 100 which is drawn or pushed through the passage 20. As is shown in FIGS. 5 and 6, when the balloon 100 is passed through the passage 20 the wall 101 of the balloon 100 will be deformed as the inward extending peaks 28 push against the wall 101 to form creases 106. The portions of the wall 101 adjacent to the creases 106 are forced into the valleys 30 to form folds 102 which extend outward from the central lumen 104. In at least one embodiment the passage 20 is configured to avoid impacting or deforming the central lumen 104 of the balloon 100. As is shown by comparing FIGS. 5 and 6, the folds 102 of the balloon 100 become more pronounced as the balloon 100 exits the narrower second opening 24 of the passage 20.

It should be understood that the passage 20 may be configured to define any combination and configuration of peaks 28 and valleys 30. By varying the height of one or more of the peaks 28 and/or one or more of the valleys 30, as well as the arrangement and number of peaks 28 and valleys 30, the passage 20 may be configured to accommodate and fold nearly any size or type of balloon. The passage may be configured to include about 3 to about 50 peaks and about 3 valleys to about 50 valleys.

In the embodiments shown, the peaks 28 may have a variety of heights as measured from the longitudinal axis 105. This height may vary between the first or larger opening 22 and the second or smaller opening 24. Peak 28 height at the first opening may range from about 2.5 mm to about 13 mm, whereas peak height at the second opening 24 may range from about 0.25 mm to about 2 mm. Similarly, the "height" of the valleys 30 as measured from the longitudinal axis 105 may be about 2.6 mm to about 15 mm at the first opening 22, and 0.26 mm to about 4 mm at the second opening 24. Thus, in at least one embodiment, the radial peak to valley distance will be about 0.1 mm to about 2.0 mm.

In regard to the peaks 28, in at least one embodiment where the tool 10 is utilized to impart folds into a balloon having a diameter of about 25 mm the height of the peaks 28 at the first opening 22 may be about 13 mm. Where the tool 10 is utilized to impart folds into a balloon having a diameter of about 4 mm, the height of the peaks at the first opening may be about 2.5 mm. However by tapering the diameter of the passage 20 or by tapering the height of the peaks 28, a single tool 10 may be utilized to impart the same fold geometry onto balloons of different diameters.

Figure 9A:
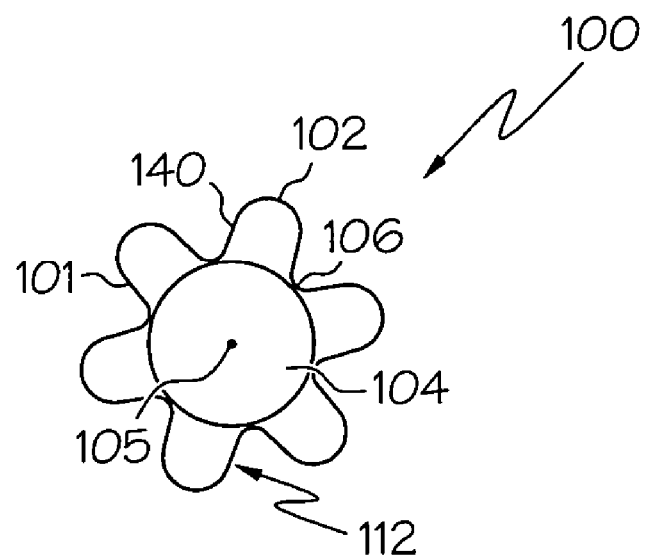
FIG. 9a is a cross-sectional view of the balloon of FIG. 7 shown subsequent to being folded by an embodiment of the folding tool.
Figure 9B:
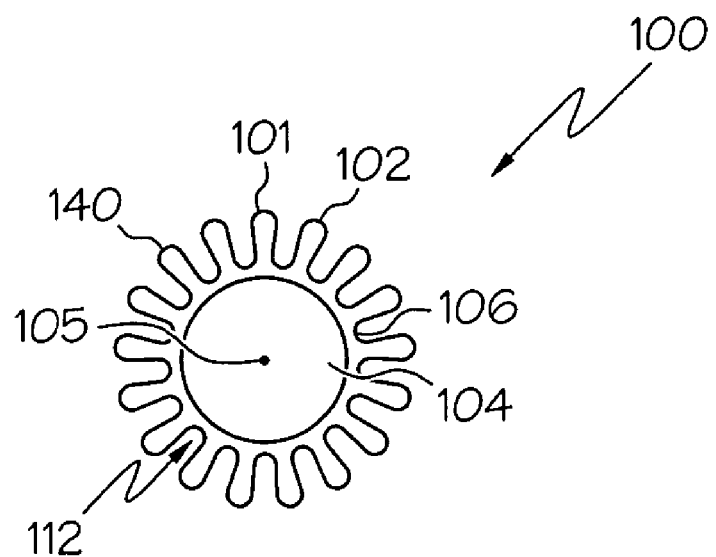
FIG. 9b is a cross-sectional view of the balloon of FIG. 7 shown subsequent to being folded by an alternative embodiment of the folding tool.

For example, as shown in FIG. 7-9b a standard angioplasty or stent delivery balloon 100 is depicted, which may be folded using the tool in the manner previously described. By varying the number of peaks 28 and valleys 30 in the passage 20, such as has been previously described, the balloon 100 may be provided with 6 folds such as is shown in FIG. 9a or any other number of folds such as 17 folds as is shown in FIG. 9b.

The tool 10 is may be constructed from a wide range of materials that are structurally suitable to provide the tool 10 with the capabilities and features described herein. Such materials are thus relatively strong, rigid, and resistant to corrosion, abrasion and wear. The material or materials from which the tool 10 is constructed are preferably suitable for the manufacture of medical devices. Such materials include but are not limited to: stainless steel, aluminum, etc. Alloys and combinations of these and other metals may also be utilized.

Figure 10:
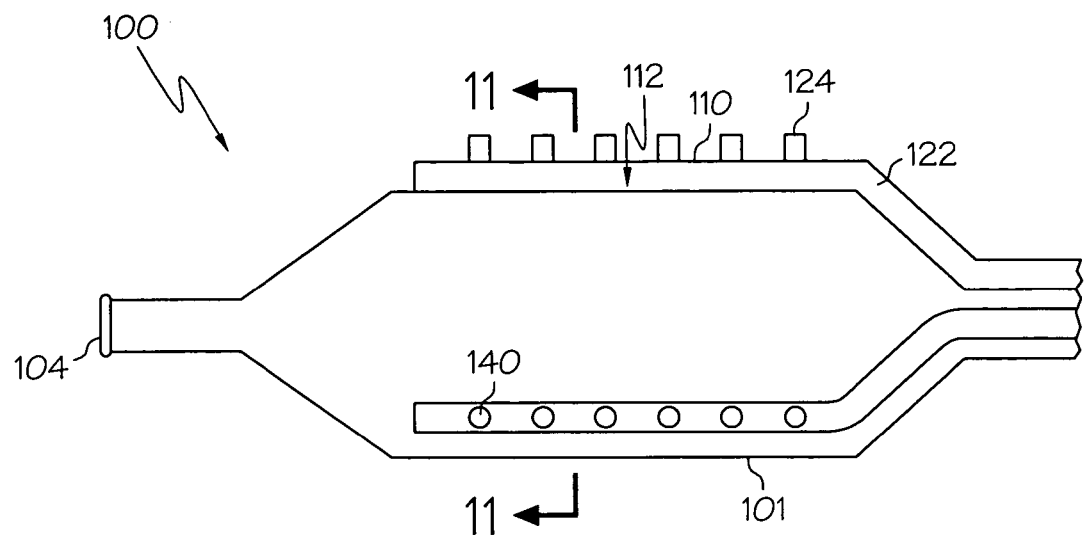
FIG. 10 is a longitudinal side view of a balloon equipped with injectors shown prior to being folded by an embodiment of the folding tool.
Figure 11:
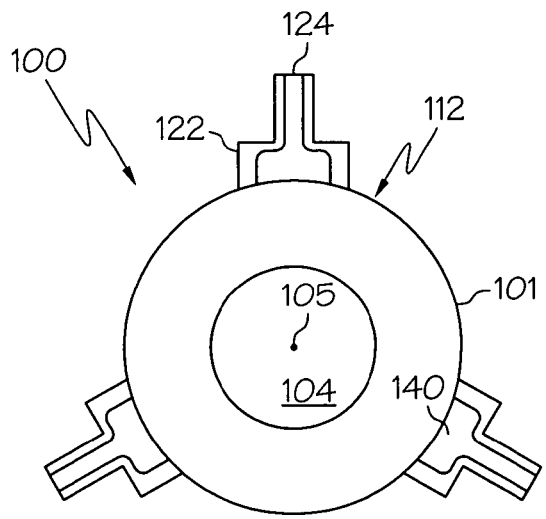
FIG. 11 is a cross-sectional view of the balloon of FIG. 10.
Figure 12:
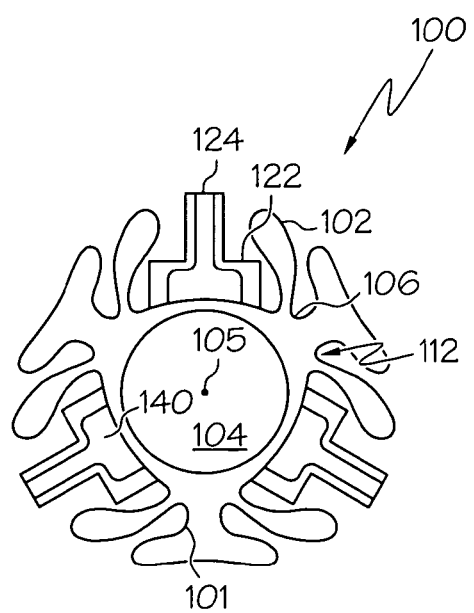
FIG. 12 is a cross-sectional view of the balloon of FIG. 10 shown subsequent to being folded by an embodiment of the folding tool.

In some embodiments the tool 10 may be configured to allow various balloon surface features, such as blades, atherotomes and/or other protrusions to be passed through the passage 20 without damaging or otherwise detrimentally affecting the surface features while still providing a desired fold configuration to the balloon. For example in at least one embodiment a balloon 100 may be equipped with a plurality of injector channels 110 on the external surface 112 of the balloon wall 101, such as is shown in FIGS. 10-12. The balloon 100 shown may be an example of the INFILTRATOR® balloon available from Interventional Technologies, Inc. of San Diego, Calif. Examples of balloons 100 may also be found in U.S. Pat. Nos. 5,112,305; 5,681,281; and 5,242,397, the entire contents of each of which are incorporated herein by reference.

The passage 20 of the tool 10, such as is shown in FIGS. 5 and 6 may be configured to provide the balloon 100 of FIGS. 10-12 with a plurality of folds, such as are shown in FIG. 12, but which allows the injectors 110 to be passed through without deformation or detrimental affects. As is shown in FIGS. 5 and 6 the passage 20 may include protrusion channels 120 which act to receive and guide the injectors 110 or other surface features on the balloon 100 through the passage 20 to allow the surface features to be repositioned into a lower profile position relative to the central lumen 104 and/or the longitudinal axis 105 of the balloon 100/passage 20, while the adjacent portion of the balloon 100 are formed into the previously described folds and creases, such as in the manner shown in FIGS. 5, 6 and 12. This reduction in profile also results in a reduced circumferential distance between the adjacent injectors 110.

In at least one embodiment, a plurality of folds 102 are provided between each of the injectors 110. The folds 102 which are adjacent to the injectors 110 may be sized to overlap the injector strip 122, but not the injector head 124.

In addition to being capable of providing folds to a balloon such as the INFILTRATOR® balloon shown in FIGS. 10-12, the tool 10 may also be configured in a similar manner for use with a balloon equipped with blades 111 and/or other surface features such as in the case of the balloon 100 shown in FIGS. 13-15b. Such a balloon 100 may be a CUTTING BALLOON® balloon available from Scimed Life Systems, Inc., of Maple Grove, Minn. Some examples of balloons and cutting blades are described in U.S. Pat. Nos. 5,320,634 and 5,616,149 the entire content of each of both being incorporated herein by reference.

Figure 13:
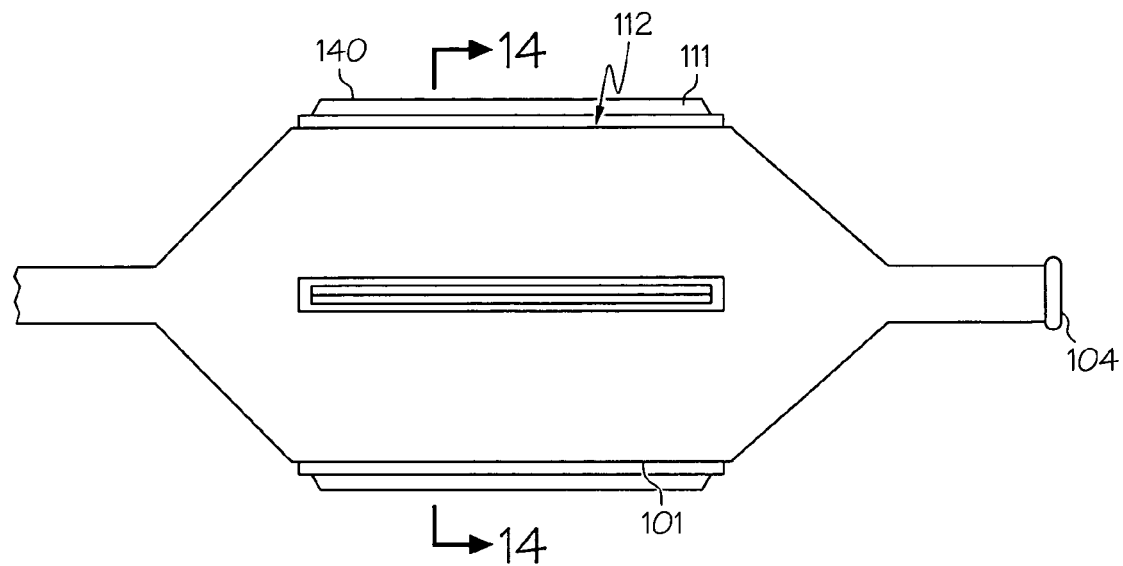
FIG. 13 is a longitudinal side view of a balloon equipped with blades shown prior to being folded by an embodiment of the folding tool.
Figure 14:
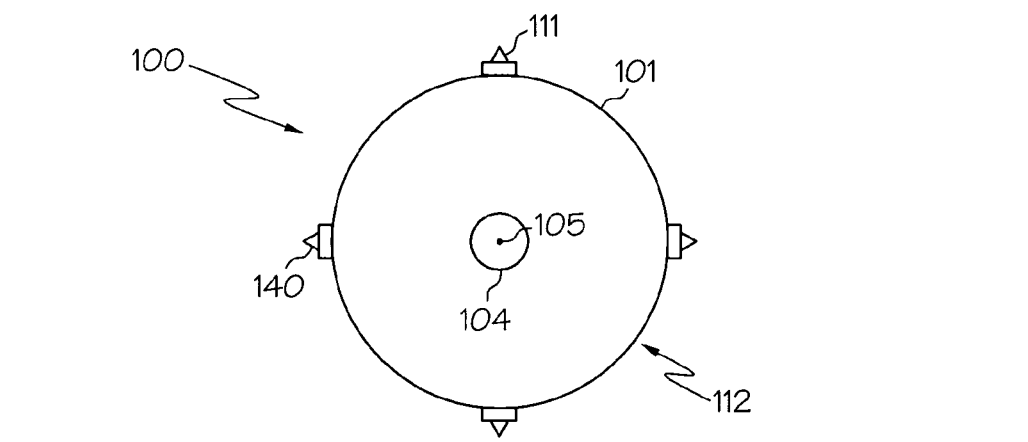
FIG. 14 is a cross-sectional view of the balloon of FIG. 13.
Figure 15A:
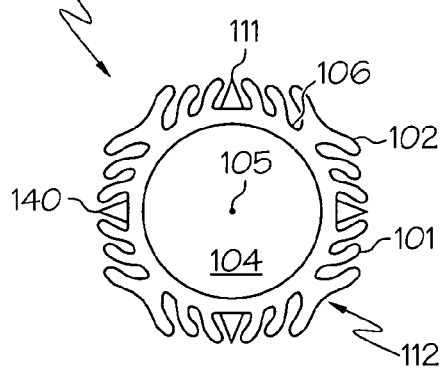
FIG. 15a is a cross-sectional view of the balloon of FIG. 13 shown subsequent to being folded by an embodiment of the folding tool.
Figure 15B:
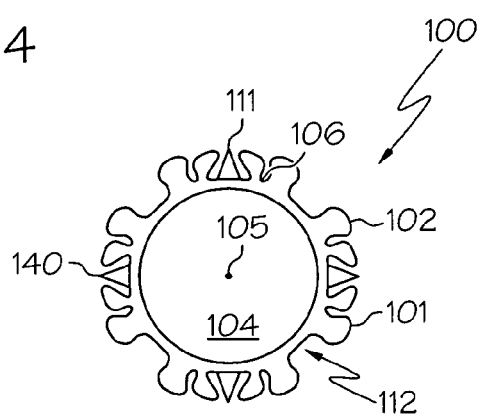
FIG. 15b is a cross-sectional view of the balloon of FIG. 13 shown subsequent to being folded by an alternative embodiment of the folding tool.

When the balloon 100 shown in FIGS. 13 and 14 is inserted into the passage 20 of the tool 10, such as is shown in FIGS. 5-6, the blades 111 are received into the protrusion channels 120. The channels 120 will cause the blades 111 to be displaced inward to a lower profile configuration such as is shown in FIGS. 15a-15b while simultaneously providing the balloon 100 with one or more folds 102 between each blade. In the example shown in FIG. 15a, the passage is configured to provide 5 folds 102 between each blade 111, whereas in the example shown in FIG. 15b three folds 102 are provided between each blade 111. As has been previously indicated, the passage 20 may be configured to provide any number of folds to the balloon as may be desired.

In at least one embodiment, such as in the example shown in FIG. 15a one or more of the folds 102 between each blade 11 has a greater profile than that of the blades to aid in protecting a vessel/lumen wall during advancement of the balloon on a catheter or other device.

In the various embodiments described herein, the tool 10 may be configured to provide a larger diameter balloon 100 with a greater number of folds than a smaller diameter balloon, as the smaller diameter balloon will have less material to fold.

Figure 16:
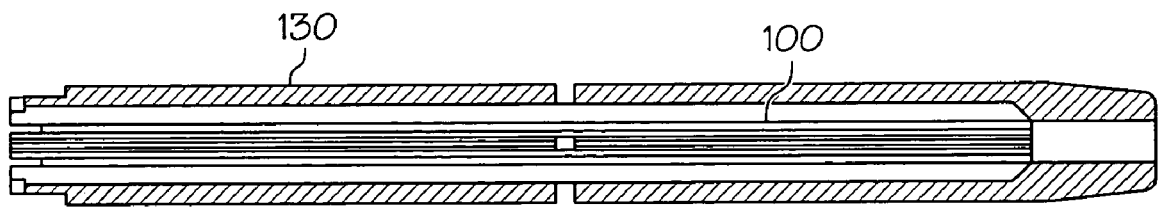
FIG. 16 is a longitudinal side view of a balloon protector into which a balloon may be advanced or placed subsequent to being folded by the folding tool.
Figure 17A:
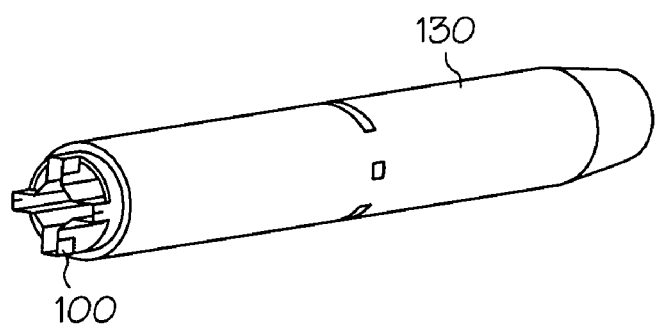
FIG. 17a is a rear perspective view of the balloon protector and balloon shown in FIG. 16.
Figure 17B:
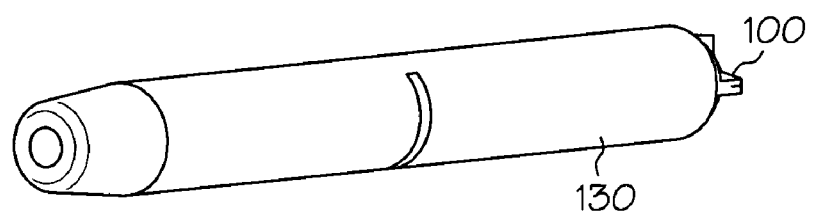
FIG. 17b is a front perspective view of the balloon protector and balloon shown in FIG. 16.

In at least one embodiment, a balloon protector 130, such as is shown in FIGS. 16-17b may be used with the tool 10, such that as the balloon 100 exits the passage 20 of the tool 10, the balloon 100 is advanced into the balloon protector or cap 130. The protector 130 is a protective tube for storing the balloon 100 in its reduced or folded state, and which also functions to protect the balloon surface, as well as any surface features such as blades, injectors, atherotomes, etc. from exposure and inadvertent contact. The balloon 100 may subsequently be removed from the protector 130 for use.

Protecting the balloon 100 from inadvertent contact and/or contamination may be especially important when the balloon 100 or at least a portion thereof is coated or otherwise equipped with one or more therapeutic agents 140, such as may be seen in the various FIGS. 5-15a A therapeutic agent 140 may be placed on the stent in the form of a coating and/or may be included in one or more surface features of the balloon (e.g. blades, injectors, atherotomes, protrusions, pores, etc). In at least one embodiment the coating includes at least one therapeutic agent and at least one polymer.

A therapeutic agent 140 can be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A tool for imparting a plurality of folds to a balloon, the tool comprising:
a housing, the housing defining a passage therethrough, the passage having a longitudinal axis, the passage having a first opening at a first end of the passage and a second opening at the second end of the passage, the passage having an inner surface, the inner surface defining a plurality of peaks and a plurality of valleys, each of the peaks having a peak height measured from the longitudinal axis, and each of the valleys having a valley height measured from the longitudinal axis, the peak height for a given peak being greater at the first end of the passage than at the second end of the passage and the valley height for a given valley is greater at the first end of the passage than at the second end of the passage, and a difference between the height of said given valley and the height of said given peak is greater at the second end of the passage than at the first end of the passage.

2. The tool of claim 1 wherein the peak height of each of the plurality of peaks is about 2.5 mm to about 13 mm at the first end.

3. The tool of claim 2 wherein the peak height of each of the plurality of peaks is about 0.25 mm to about 2 mm at the second end.

4. The tool of claim 3 wherein the valley height of each of the plurality of valleys is about 2.6 mm to about 15 mm at the first end.

5. The tool of claim 4 wherein the valley height of each of the plurality of valleys is about 0.26 mm to about 4 mm at the second end.

6. The tool of claim 1 wherein the first opening is larger than the second opening.

7. The tool of claim 1 wherein the housing comprises a first segment and a second segment, the first segment and the second segment being moveably engaged, the first segment defining a first region of the inner surface of the passage and the second segment defining a second region of the inner surface of the passage, the passage being formed when the first segment and the second segment are engaged together.

8. The tool of claim 7 wherein the first segment and the second segment are engaged together about a pivot member, the first region of the inner surface of the passage, and the second region of the inner surface of the passage being pivotally moveable relative to one another.

9. The tool of claim 1 wherein the inner surface of the passage comprises about 3 to about 50 peaks and about 3 to about 50 valleys.

10. The tool of claim 1 wherein the inner surface of the passage further defines at least one protrusion channel, the at least one protrusion channel comprising a valley having a predetermined cross-sectional shape that is different from other valleys, said predetermined cross-sectional shape extending the length of the passage, the at least one protrusion channel constructed and arranged to receive at least one protrusion positioned on a balloon, the at least one protrusion channel further constructed and arranged to bias the at least one protrusion radially inward toward the longitudinal axis.

11. A method of imparting folds to a balloon comprising:
providing a folding tool, the folding tool comprising a housing, the housing defining a passage therethrough, the passage having a longitudinal axis, the passage having a first opening at a first end of the passage and a second opening at the second end of the passage, the passage having an inner surface, the inner surface defining a plurality of peaks and a plurality of valleys, each of the peaks having a peak height measured from the longitudinal axis, and each of the valleys having a valley height measured from the longitudinal axis, the peak height for a given peak being greater at the first end of the passage than at the second end of the passage and the valley height for a given valley is greater at the first end of the passage than at the second end of the passage, and a difference between the height of said given valley and the height of said given peak is greater at the second end of the passage than at the first end of the passage.

12. The method of claim 11 comprising the step of:
imparting a plurality of creases in the balloon, each crease being imparted to the balloon where each peak contacts the balloon during advancement of the balloon through the passage.

13. The method of claim 12 comprising the step of:
imparting a plurality of folds in the balloon, each of the folds being a portion of the balloon that is directed into one of the valleys as a result of the contact of the peaks against the balloon during advancement of the balloon through the passage.

14. The method of claim 13 wherein during the advancement of the balloon through the passage, the balloon is inflated to a pressure of about 0.5 psig to about 20 psig.

15. The method of claim 11 wherein the balloon comprises at least one therapeutic agent.

16. The method of claim 11 wherein the balloon comprises an external surface and at least one protrusion engaged to the external surface.

17. The method of claim 16 wherein the at least one protrusion is selected from the group consisting of: injectors, blades, atherotomes and any combinations thereof.

18. The method of claim 17 wherein the inner surface of the passage further defines at least one protrusion channel, the at least one protrusion channel constructed and arranged to receive the at least one protrusion, such that during advancement of the balloon through the passage the at least one protrusion channel biases the at least one protrusion radially inward toward the longitudinal axis.

19. The method of claim 11 wherein the inner surface of the passage comprises about 3 to about 50 peaks and about 3 to about 50 valleys.

20. The method of claim 11 further comprising the step of removing the balloon from the second opening of the passage, the balloon being imparted with a plurality of folds.

21. The method of claim 20 wherein when the balloon is removed from the second opening of the passage, the balloon is inserted into a balloon protector tube, the balloon protector tube retaining the balloon in a folded configuration.

22. A system for imparting a plurality of folds to a balloon, the system comprising:
a folding tool, the folding tool having a housing, the housing defining a passage therethrough, the passage having a longitudinal axis, the passage having a first opening at a first end of the passage and a second opening at the second end of the passage, the passage having an inner surface, the inner surface defining a plurality of peaks and a plurality of valleys, each of the peaks having a peak height measured from the longitudinal axis, and each of the valleys having a valley height measured from the longitudinal axis, the peak height for a given peak being greater at the first end of the passage than at the second end of the passage and the valley height for a given valley is greater at the first end of the passage than at the second end of the passage, and a difference between the height of said given valley and the height of said given peak is greater at the second end of the passage than at the first end of the passage;
a balloon, the balloon having a balloon body and defining a central lumen about a balloon longitudinal axis, the balloon having a prefolded state and a folded state, in the prefolded state the balloon body being a substantially uniform distance from the balloon longitudinal axis, in the folded state the balloon having a plurality of distinct folds extending outward from the balloon longitudinal axis, the balloon being in the prefolded state prior to being advanced through the passage, and in the folded state following advancement of the balloon through the passage; and
a balloon protector, the balloon protector comprising a substantially hollow tubular member, the balloon in the folded state being positioned within the balloon protector.

* * * * *